United States Patent
MoodyCliffe et al.

(10) Patent No.: US 7,048,205 B2
(45) Date of Patent: May 23, 2006

(54) LAVATORY FRESHENING AND/OR CLEANING SYSTEM AND METHOD

(75) Inventors: Timothy I. MoodyCliffe, Milwaukee, WI (US); Jerome J. Veltman, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 180 days.

(21) Appl. No.: 10/332,599

(22) PCT Filed: Jul. 11, 2001

(86) PCT No.: PCT/US01/21788

§ 371 (c)(1),
(2), (4) Date: Aug. 4, 2003

(87) PCT Pub. No.: WO02/04591

PCT Pub. Date: Jan. 17, 2002

(65) Prior Publication Data

US 2004/0049839 A1    Mar. 18, 2004

(30) Foreign Application Priority Data

Jul. 12, 2000    (GB) .................... 0017154.6

(51) Int. Cl.
*A62C 13/62*    (2006.01)
*A62C 13/66*    (2006.01)
*A62C 5/02*    (2006.01)
*A01G 25/14*    (2006.01)

(52) U.S. Cl. ............... 239/302; 239/310; 239/316; 239/375

(58) Field of Classification Search ........... 239/302, 239/310, 316, 375; 4/223, 231, 230, 224; 510/416, 221, 226, 434, 490

See application file for complete search history.

(56) References Cited

U.S. PATENT DOCUMENTS

| 4,678,606 A |   | 7/1987  | Akhter et al. ............ 252/542 |
|-------------|---|---------|------------------------------------|
| 4,777,670 A | * | 10/1988 | Klinkhammer et al. ...... 4/231   |
| 4,783,283 A | * | 11/1988 | Stoddart ............... 510/373   |
| 4,813,084 A | * | 3/1989  | Buecheler et al. ........ 4/231   |
| 5,916,967 A | * | 6/1999  | Jones et al. ............ 524/732 |
| 6,013,615 A | * | 1/2000  | Zhou et al. ............. 510/434 |
| 6,121,227 A | * | 9/2000  | Meine et al. ............ 510/416 |
| 6,178,564 B1| * | 1/2001  | Leonard et al. .......... 4/223   |

FOREIGN PATENT DOCUMENTS

| EP | 0775741 A1   | 5/1997  |
| EP | 0920860 A2   | 6/1999  |
| EP | 1029911 A1   | 8/2000  |
| WO | WO 98/46712  | 10/1998 |
| WO | WO 99/66139  | 12/1999 |
| WO | WO 00/29532  | 5/2000  |
| WO | WO 00/53718  | 9/2000  |
| WO | WO 01/44591 A1 | 6/2001 |

OTHER PUBLICATIONS

WPI Abstract Accession No. 1985-193166 [32] & JP 600119950 A (Johnson Corp) See abstract.

* cited by examiner

*Primary Examiner*—Davis Hwu

(57) ABSTRACT

A lavatory freshening and/or cleaning system comprises a dispenser for dispensing a liquid composition from under the rim of a lavatory bowl. The dispenser is in the form of a reservoir arranged for suspension from the rim of lavatory bowl, and the reservoir contains the liquid composition. The liquid composition comprises a combination of anionic and non-ionic surfactants having a total concentration of 22.5 wt. %, a thickening agent having a concentration of 0.40 wt. % and a perfume having a concentration of 6.00 wt. % and having a viscosity of a bout 3,500 mPa s.

18 Claims, No Drawings

LAVATORY FRESHENING AND/OR CLEANING SYSTEM AND METHOD

This invention relates to a freshener and/or cleaner system for the lavatory and to a method of using such a system in a lavatory bowl. In particular, this invention relates to a system comprising a liquid freshening and/or cleaning composition and a liquid dispenser.

Several lavatory freshening and/or cleaning systems are known. These systems include "solid block" type systems, where a freshening and/or cleaning block is placed either under the rim of the lavatory or in the cistern. In the case of the under the rim system, water dissolves part of the block each time the lavatory is flushed, allowing the lavatory bowl to be cleaned and/or freshened. In the case of the cistern block system, part of the block dissolves in the cistern prior to flushing and the toilet is cleaned and freshened on flushing of the water held in the cistern into the lavatory bowl. However, solid toilet blocks have demonstrated several drawbacks, in particular their inability to deliver constant amounts of cleaning and freshening agents during the lifetime of the block.

Other freshening and cleaning systems are of the liquid-dispensing type. Such systems include a liquid dispenser and a liquid freshening and/or cleaning composition. A liquid dispenser suitable for such a system is disclosed in the applicant's published international patent application WO 99/66139. Such liquid dispensers generally comprise a reservoir and a liquid-conveying device in the form of a pad, or a plate having capillary channels formed therein, the liquid-conveying device and the reservoir being so connected as to allow the freshening and/or cleaning composition held in the reservoir to be transferred to the liquid-conveying device in a controlled manner. The liquid dispenser is positioned under the rim of a lavatory such that, during flushing, a sufficient amount of freshening and/or cleaning composition is transferred to the lavatory bowl to effect the cleaning of the bowl.

In order for liquid cleaning systems to be effective, the liquid dispenser must be provided with a suitable liquid cleaning and/or freshening composition. It is desirable that such a liquid composition possess certain properties in order to carry out its freshening and/or cleaning functions. In particular, it is desirable that, when the composition is dispensed by flushing, sufficient foaming occurs. Foaming is desirable in order to promote cleaning of the lavatory bowl and dispersal of any perfume which is contained in the composition. Foaming also confers certain aesthetic properties when the toilet is flushed.

A known liquid cleaning composition, stated to be suitable for liquid cleaning systems of the type hereinbefore described, is disclosed in European patent application EP-A-0 775 741, which describes a composition having a viscosity at room temperature of 10 to 2 000 mPa s and comprising:

(a) 1 to 25 wt. % of perfume,
(b) 10 to 50 wt. % of anionic or non-ionic surfactant,
(c) 1 to 20 wt. % of non-evaporating, water soluble evaporation regulator, and
(d) balance solvent.

As used herein, the term "viscosity" refers to the dynamic viscosity, as measured using a Brookfield viscometer (spindle no. 3, 12 rpm, 30 seconds at 20° C.). The above range of values for the viscosity is believed to be typically used for reasons of economy and ease of manufacture.

However, dispensers incorporating such liquids have been found, under certain circumstances, to draw the flushing water into the reservoir. This effect can lead to a reduction in the concentration of the active components in the liquid contained in the reservoir, and hence a corresponding reduction in the quantity of the active components transferred to the lavatory bowl, over the lifetime of the reservoir. In particular, this is manifested by reduced foaming and/or fragrance release.

The present inventors have discovered that, by substantially increasing the viscosity of the liquid composition, these undesirable effects can be reduced substantially, or even eliminated.

Thus, in accordance with the present invention, there is provided a lavatory freshening and/or cleaning system comprising a dispenser for dispensing a liquid composition from under the rim of a lavatory bowl, said liquid composition having a viscosity greater than 2 500 mPa s.

The viscosity is preferably less than 6 000 mPa s and more preferably within the range 3 000 to 5 000 mPa s. The most preferred value is about 3 500 mPa s.

Typically, such liquid compositions would include surfactants. Surfactants carry out a variety of functions, inter alia, generating of foam during the flush and dissolving or micro-emulsifying any perfume present in the liquid composition.

Preferably, the total surfactant concentration is within the range 5 to 35 wt. %, the most preferred value being substantially 22.5 wt. %.

Suitable surfactants are anionic and/or non-ionic surfactants, although a combination of anionic and non-ionic surfactants is particularly desirable. The preferred anionic surfactant is an alkyl ether sulphate, such at that marketed under the trade name Steol CS 270, containing active surfactant at a concentration of 70 wt. %, and the preferred non-ionic surfactant is an ethoxylated synthetic alcohol, such as that marketed under the trade name Lutensol AO8.

Optionally, perfume may be present to provide freshening of the lavatory bowl and its vicinity. A suitable perfume for the liquid composition is that marketed under the trade name Vertana 114.737.

The preferred total concentration of perfume is within the range 4 to 15 wt. %, the most preferred value being substantially 6 wt. %.

Although the combination of surfactant and perfume can act as a thickening agent, and thus the viscosity of the composition may be controlled to an extent by the choice of surfactants and/or perfume, the composition preferably includes one or more additional thickening agents, having a preferred total concentration within the range 0.2 to 20 wt %. The most preferred concentration of additional thickening agent is substantially 0.40 wt %. A suitable thickening agent is a hydroethylcellulose such as that marketed under the trade name Natrasol 250 HHR.

In addition, humectants may be present in the liquid composition. Humectants are desirable when a perfume is present, in order to regulate the evaporation of the perfume from the composition. Additionally, humectants are useful in preventing phase separation of, and precipitation from, the composition.

Suitable humectants include glycols, glycoethers, alcohols, sugars and polyethers.

Optionally, the composition may comprise sequestrants, pH control agents, dyes and preservatives.

The invention extends to a method of use of such a lavatory freshening and/or cleaning system in a lavatory bowl.

A preferred embodiment of the present invention incorporates a liquid composition having the following components:

| Weight percent | Common name | Chemical name | Component type | Function |
|---|---|---|---|---|
|  | Water | Water |  | Solvent |
| 25 | Steol CS 270 (containing 70% active surfactant) | Sodium Lauryl Ether Sulphate | Anionic surfactant | Perfume solublisation, form generation and viscosity building |
| 5.0 | Lutensol AO8 |  | Non-ionic surfactant | Perfume solublisation, form generation and viscosity building |
| 7.00 |  | Dipropylene Glycol | Short-chain hydrocarbon | Humectant |
| 2.00 | Dequest 2010 |  | Phosphonate | Sequestrant |
| 1.60 |  | Sodium Hydroxide (32 wt. % aqueous solution) |  | Control of pH |
| 0.40 | Natrasol 250 HHR |  | Cellulosic | Thickener |
| 0.005 |  |  |  | Dye |
| 6.00 |  |  |  | Perfume |
| 0.02 | Myacide BT |  |  | Preservative |

As can be seen from the above table, the composition comprises Steol CS 270. This includes an anionic surfactant at a concentration of 70 wt. %, so that the actual concentration of anionic surfactant in the composition is 17.5 wt. %, resulting in a total surfactant concentration in the composition of 22.5 wt. %.

The resulting viscosity of the above liquid composition is about 3 500 mPa s.

The invention claimed is:

1. A lavatory freshening and/or cleaning system comprising a dispenser for dispensing a liquid composition from under the rim of a lavatory bowl and said liquid composition having a viscosity greater than 3,000 mPa s at 20° C.

2. A system as claimed in claim 1, wherein said liquid composition has a viscosity less than 6,000 mPa s at 20° C.

3. A system as claimed in claim 2, wherein said liquid composition has a viscosity within the range 3,000 to 5,000 mPa s at 20° C.

4. A system as claimed in claim 3, wherein said liquid composition has a viscosity of about 3,500 mPa s at 20° C.

5. A system as claimed in claim 1, wherein said liquid composition comprises a surfactant.

6. A system as claimed in claim 5, wherein the total surfactant concentration is within the range 5 to 35 wt. %.

7. A system as claimed in claim 6, wherein the total surfactant concentration is substantially 22.5 wt. %.

8. A system as claimed in claim 5, wherein said surfactant is either an anionic surfactant or a non-ionic surfactant or a combination thereof.

9. A system as claimed in claim 8, comprising an alkyl ether sulphate constituting at least one anionic surfactant.

10. A system as claimed in claim 8, comprising an ethoxylated synthetic alcohol constituting at least one non-ionic surfactant.

11. A system as claimed in claim 1, wherein said liquid composition further comprises perfume.

12. A system as claimed in claim 11, wherein the total perfume concentration is within the range 4 to 15 wt. %.

13. A system as claimed in claim 11, wherein the total perfume concentration is substantially 6 wt. %.

14. A system as claimed in claim 1, wherein said liquid composition comprises a thickening agent.

15. A system as claimed in claim 1, wherein said liquid composition further comprises one or more of sequestrants, pH control agents, dyes and preservatives.

16. A method of using in a lavatory bowl a lavatory freshening and/or cleaning system as claimed in claim 1.

17. A lavatory freshening and/or cleaning system comprising a dispenser for dispensing a liquid composition from under the rim of a lavatory bowl and said liquid composition, said liquid composition comprising a thickening agent and having a viscosity greater than 2,500 mPa s at 20° C., wherein the concentration of thickening agent, apart from any surfactant and perfume which may be present, is within the range 0.2 to 5 wt. %.

18. A lavatory freshening and/or cleaning system comprising a dispenser for dispensing a liquid composition from under the rim of a lavatory bowl and said liquid composition, said liquid composition having a viscosity greater than 3,000 mPa s at 20° C., wherein said thickening agent is a hydroxyethylcellulose.

* * * * *